(12) United States Patent
Narasimhan et al.

(10) Patent No.: US 11,406,813 B2
(45) Date of Patent: Aug. 9, 2022

(54) STIMULATION PROBE ASSEMBLIES AND METHODS OF USE

(71) Applicant: MEDTRONIC XOMED, INC., Jacksonville, FL (US)

(72) Inventors: Anirudhan Narasimhan, Chicago, IL (US); David C. Hacker, Jacksonville, FL (US); Kevin L. McFarlin, Jacksonville, FL (US); Gabriela A. Guillen, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 277 days.

(21) Appl. No.: 16/595,160

(22) Filed: Oct. 7, 2019

(65) Prior Publication Data

US 2020/0121916 A1     Apr. 23, 2020

Related U.S. Application Data

(60) Provisional application No. 62/748,594, filed on Oct. 22, 2018.

(51) Int. Cl.
*A61N 1/04* (2006.01)
*A61N 1/05* (2006.01)
*A61N 1/36* (2006.01)

(52) U.S. Cl.
CPC ......... *A61N 1/0496* (2013.01); *A61N 1/0539* (2013.01); *A61N 1/3605* (2013.01)

(58) Field of Classification Search
CPC .. A61N 1/0496; A61N 1/0539; A61N 1/3605; A61N 1/0558; A61N 1/0502
See application file for complete search history.

(56) References Cited

U.S. PATENT DOCUMENTS

| 5,776,144 A * | 7/1998 | Leysieffer | A61F 11/004 600/25 |
| 6,752,812 B1 * | 6/2004 | Truwit | A61B 90/11 606/1 |

(Continued)

FOREIGN PATENT DOCUMENTS

| WO | 03015867 | 2/2003 |
| WO | 2015179878 | 11/2015 |
| WO | 2017066734 | 4/2017 |

OTHER PUBLICATIONS

The International Search Report and Written Opinion for International Application No. PCT/US2019/055037 dated Jan. 7, 2020 (12 pages).

*Primary Examiner* — Rex R Holmes
(74) *Attorney, Agent, or Firm* — Dicke, Billig & Czaja, PLLC

(57) ABSTRACT

Aspects of the disclosure include a bio-electric stimulation probe assembly including a patch including a first aperture and also a guide socket including a grommet and a second aperture. The guide socket is positioned on the patch such that the first and second apertures are aligned. The assembly further includes a guide including a tip that is positioned within and rotatable within the grommet. A probe of the assembly having at least one electrode is interconnected with the guide and extends through the first and second apertures. The guide and guide socket are collectively arranged and configured so that the guide has three degrees of rotational freedom with respect to the grommet thus meaning the probe correspondingly has three degrees of rotational freedom with respect to the grommet. Methods of using stimulation probe assemblies are also disclosed.

20 Claims, 7 Drawing Sheets

(56) References Cited

U.S. PATENT DOCUMENTS

2003/0195599 A1* 10/2003 Bishay ............... A61N 1/36021
607/116
2017/0340891 A1* 11/2017 Boggs ................ A61B 17/3468
2018/0153474 A1    6/2018 Aeschlimann et al.

* cited by examiner

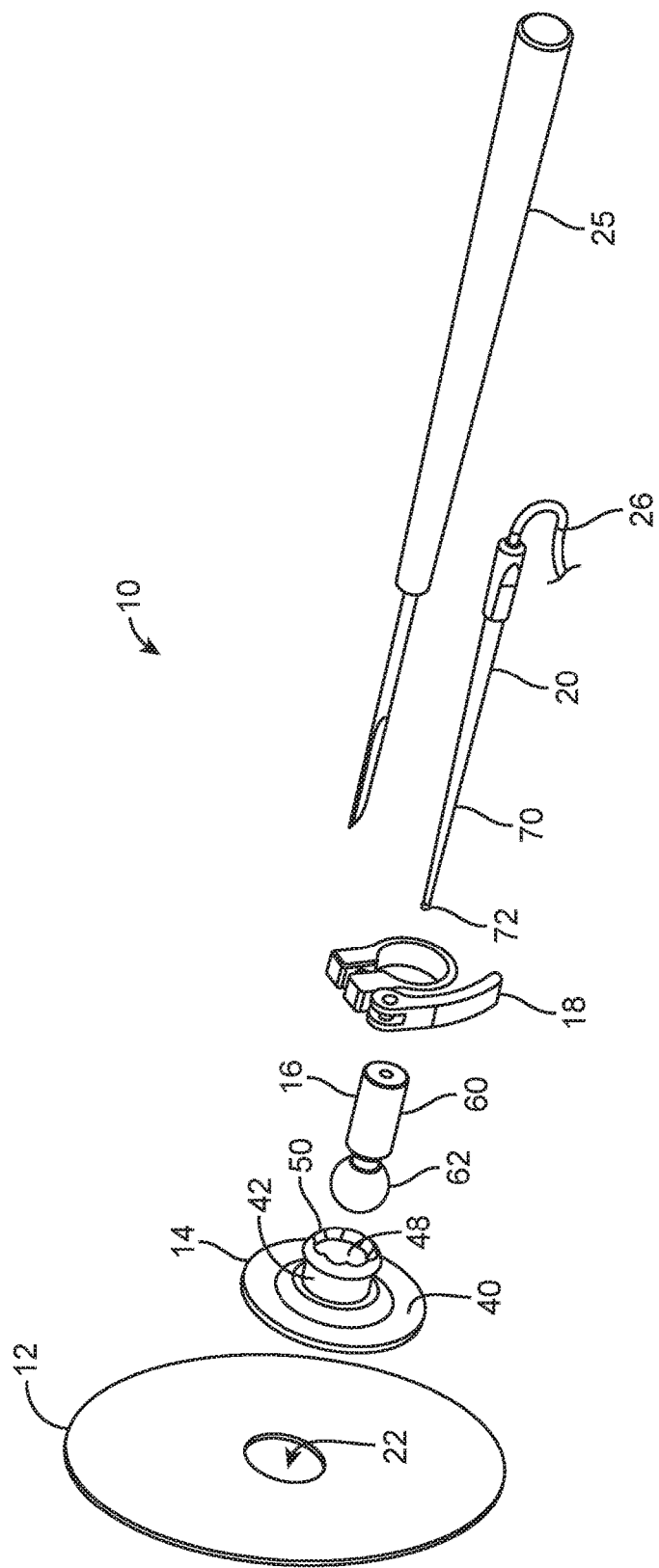
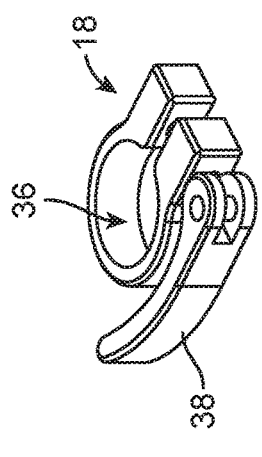
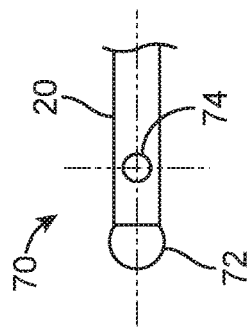
FIG. 4
FIG. 6
FIG. 5

STIMULATION PROBE ASSEMBLIES AND METHODS OF USE

CROSS REFERENCE TO RELATED APPLICATIONS

This Non-Provisional Patent Application claims the benefit of the filing date of U.S. Provisional Patent Application Ser. No. 62/748,594, filed Oct. 22, 2018, entitled "STIMULATION PROBE ASSEMBLIES AND METHODS OF USE," the entire teachings of which are incorporated herein by reference.

FIELD

The present technology is generally related to devices and methods for bioelectric tissue (e.g., nerve) stimulation and monitoring.

BACKGROUND

Head and neck surgeries, for the treatment of head and neck cancer, sinus disease, thyroid and parathyroid disorders, tonsil and adenoid conditions, for example, frequently incorporate intraoperative nerve monitoring of the recurrent laryngeal nerve, vagus nerve or other motor nerves are common. Known nerve monitoring systems enable surgeons to identify and confirm motor nerve function and monitor major motor nerves during surgery. If there is a change in nerve function, the nerve monitoring system may provide visual and audible warnings to alert the surgeon. This helps reduce the risk of intraoperative nerve damage during such procedures. Active monitoring with percutaneous stimulation can aid in the safety and effectiveness of ablative treatments or therapies for example: alcohol ablation, radiofrequency ablation, radioactive ablation, percutaneous laser ablation, thermal hyperthermia ablation or thermal hypothermia ablation, and high-intensity focused ultrasound ablation. Monitoring with intermittent percutaneous stimulation can aid in locating neuro structures can aid in directing ablation therapy away from nerve structures. Continuous nerve monitoring with percutaneous stimulation can aid in assessing nerve activity to actively titrate/regulate of ablation therapies to minimize unintended nerve damage.

The present disclosure addresses problems and limitations associated with the related art.

SUMMARY

The techniques of this disclosure generally relate to devices and methods of for bioelectric tissue stimulation and monitoring. Various aspects of the disclosure are particularly useful for stimulating and monitoring for head and neck surgical procedures and stimulation or monitoring of a patient's nerve, such as a vagus nerve, cranial nerve, peripheral nerve or nerve root. Obtaining consistent laryngeal electromyography (EMG) data with an EMG endotracheal (ET) tube can be challenging during head and neck procedures because stimulating a nerve manually with a probe is time consuming or placing a continuous monitoring electrode (APS) around a nerve is evasive requiring a high degree of surgical skill. Also, the contact between the EMG ET tube surface electrodes and a patient's larynx frequently changes during the course of the procedure. Such movement forces the surgeon need to use the stimulation probe while manipulating the EMG ET tube every time there is doubt in the result to rule out potential false negatives. Various embodiments of the disclosure provide for a stimulation and monitoring electrode that allows surgeons to stimulate a nerve and continuously monitor the nerve through a minimally invasive approach.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 4 is an exploded view of the stimulation probe assembly of FIGS. 2-3 and further including a blade.

FIG. 5 is an enlarged view of an end of a probe of the stimulation probe assembly of FIGS. 1-4.

FIG. 6 is a perspective view of the clamp of FIGS. 1-4.

DETAILED DESCRIPTION

Figure 1:
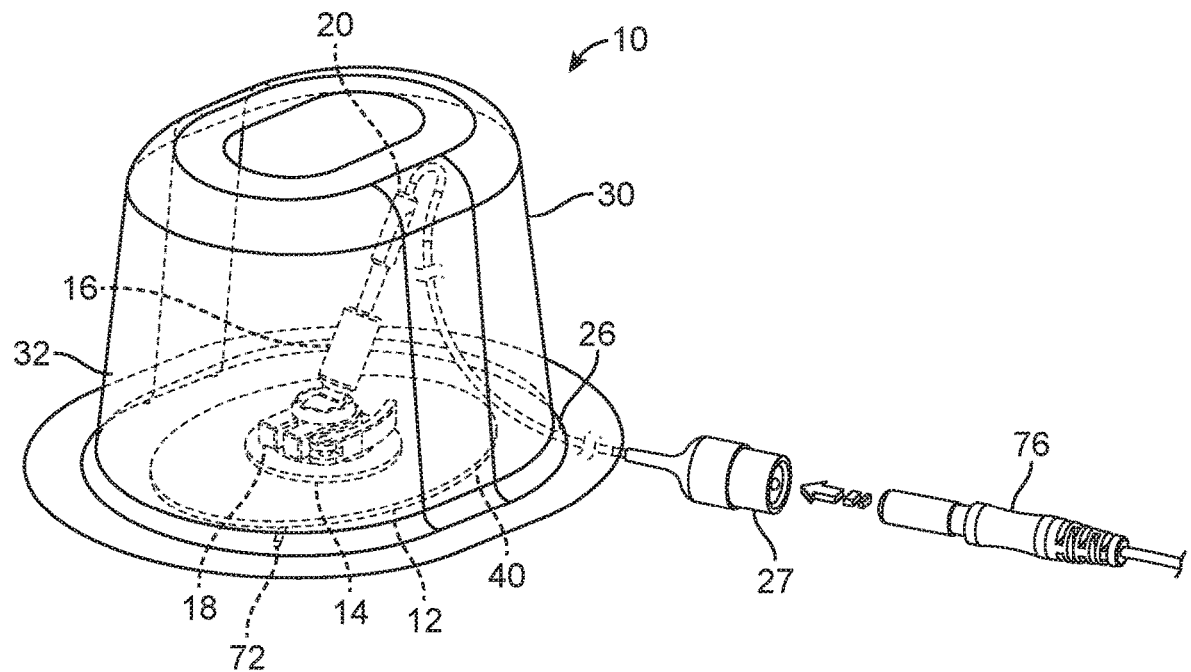
FIG. 1 is a perspective view of a stimulation probe assembly that illustrates a patch, guide socket, probe guide, clamp, probe and cup; wherein the stimulation probe assembly can be connected to a nerve monitoring system (schematically shown).
Figure 2:
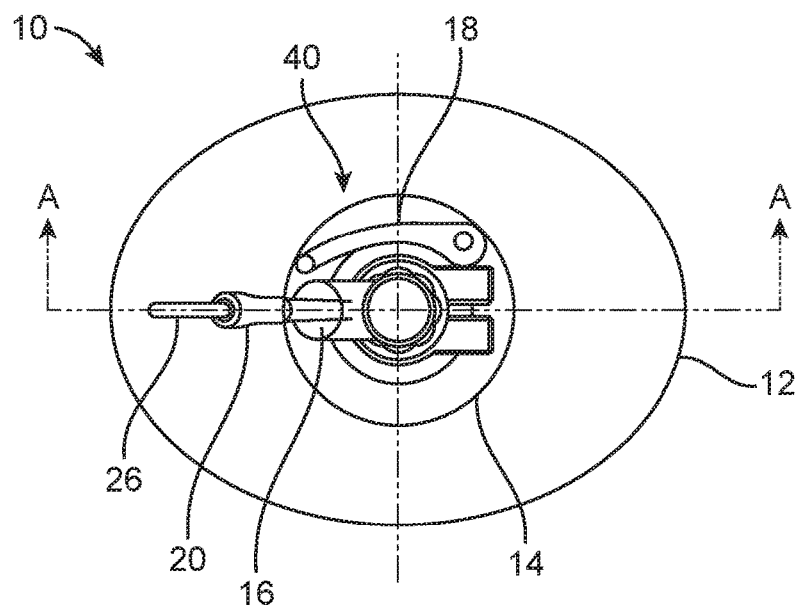
FIG. 2 is a top view of the stimulation probe assembly of FIG. 1 having the cup omitted for ease of illustration.
Figure 3:
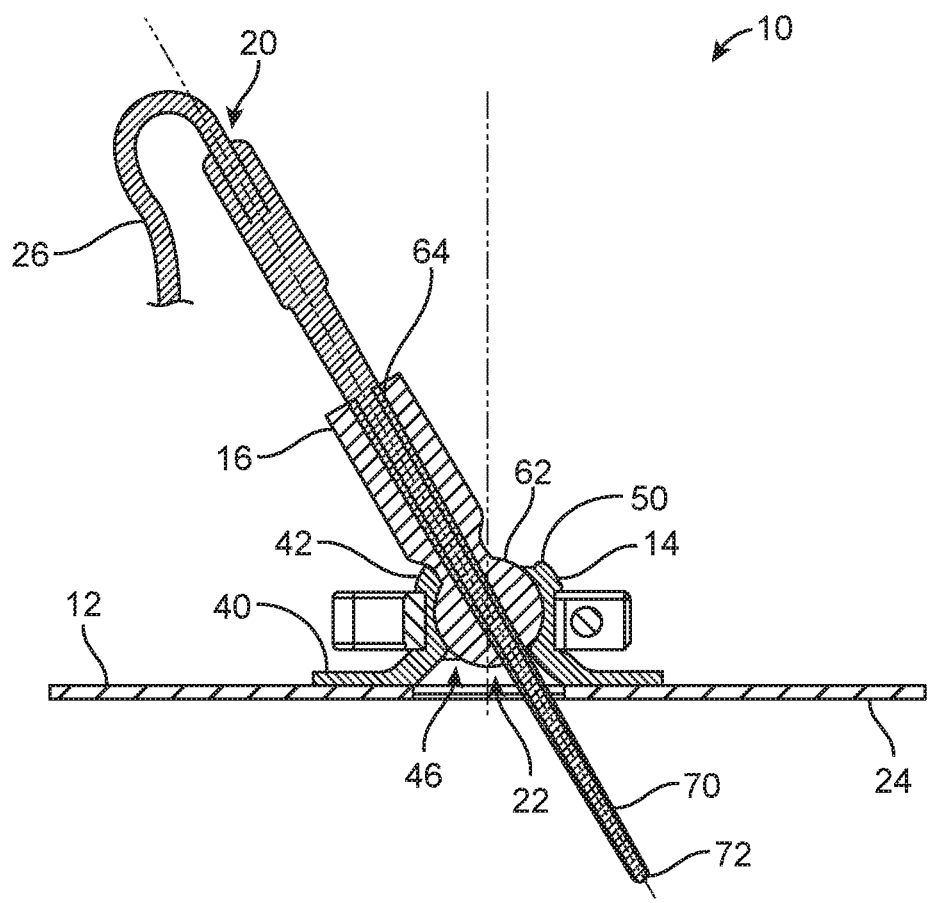
FIG. 3 is a cross-sectional view of the stimulation probe assembly of FIG. 2 as viewed along line A-A.
Figure 7:
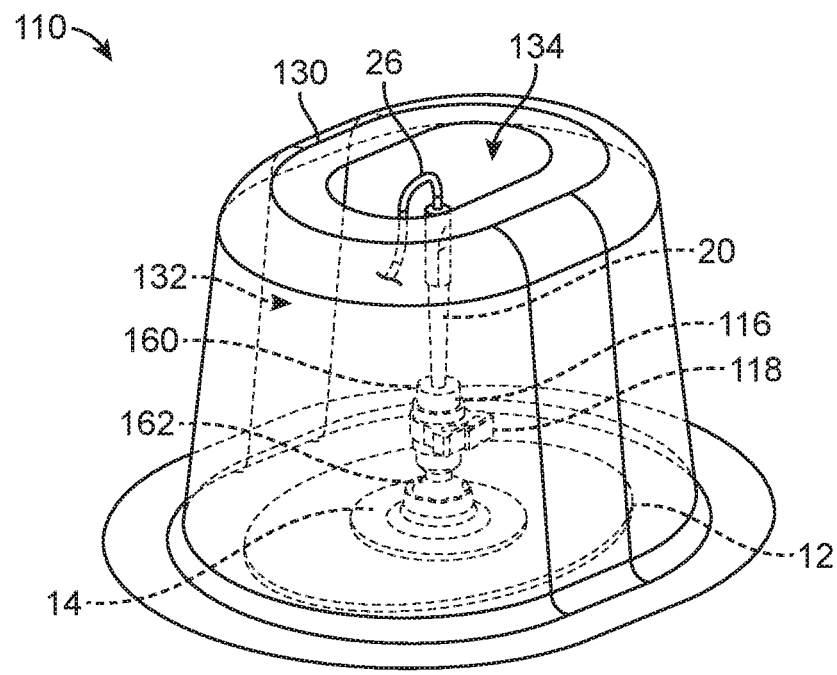
FIG. 7 is a perspective view of an alternate simulation probe assembly that illustrates a patch, guide socket, probe guide, clamp, probe and cup.
Figure 8:
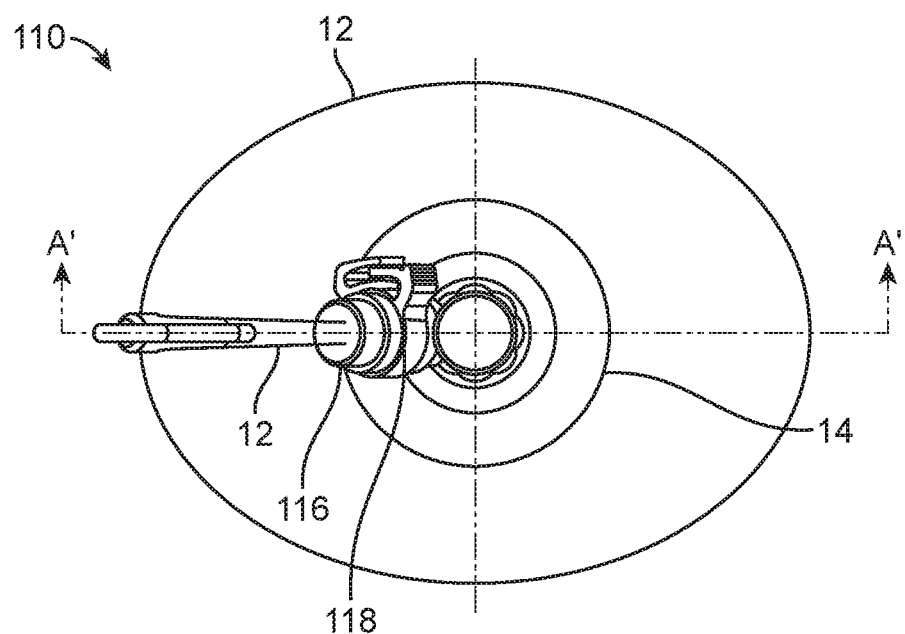
FIG. 8 is a top view of the stimulation probe assembly of FIG. 7 having the cup omitted for ease of illustration.

FIGS. 1-6 collectively illustrate a stimulation probe assembly 10 in accordance with aspects of the present disclosure. The stimulation probe assembly 10 includes a patch 12, guide socket 14, probe guide 16, clamp 18 and probe 20. The patch 12 includes a first aperture 22, which can be used in combination with a blade 25 (FIG. 4) to form an incision in a patient's skin for insertion of the probe 20. Alternatively, the incision can be formed in any known manner prior to application of the stimulation probe assembly 10 and in other embodiments, the stimulation probe assembly 10 is used in a transcutaneous manner. The patch 12 can be made of a flexible material and include an adhesive layer (generally represented at 24 in FIG. 3), which can secure the stimulation probe assembly 10 to a patient's skin (not shown).

Optionally, the stimulation probe assembly 10 can further include a cup 30 as illustrated in FIG. 1. The cup 30 has a recess 32 that is positioned over the patch 12, guide socket 14, probe guide 16, clamp 18 and probe 20 (with the exception of a wiring assembly 26 for the probe 20 as illustrated in FIG. 1), to prevent any accidental bumping or unintended repositioning of the probe 20 when in use. In some embodiments, the cup 30 is provided with a flange 34 for removably securing to the patient with adhesive of the like similar to the patch 12 (not shown). The stimulation probe assembly 10 is configured to be in communication with a nerve monitoring system 76, only part of which is shown (e.g., NIM Eclipse® (part number 945NCCPUE4), NIM-Response® 3.0 (part number 8253001) and NIM-Neuro® 3.0 nerve (part number 8253401) monitoring systems all available from Medtronic, Inc. of Minneapolis, Minn.). In some embodiments, the stimulation probe assembly 10 is in communication with the nerve monitoring system 76 via wiring assembly 26. The wiring assembly 26 wire can optionally include a detachable connector 27 so that a nerve monitoring system can be separated and rejoined to the probe 20 to aid in delivery.

The guide socket 14 includes a flange 40 extending from a socket 42. The flange 40 includes a second aperture 46 that is in communication with a grommet 48 formed by the socket 42. The guide socket 14 is secured to the patch such that the first and second apertures 22, 46 are aligned, around the incision (see, in particular, FIG. 3). The socket 42 can proximally terminate at an edge 50, which can be irregular and include one or more divots to assist in maintaining the probe 20 in the desired position.

The probe guide 16 includes a body 60 distally terminating at a guide tip 62 that is positioned within and rotatable within the grommet 48 of the guide socket 14. In this way, the guide tip 62 can be spherically shaped so that the guide tip 62 and grommet 48 collectively form a ball and socket joint. In this way, the guide tip 62 can rotate 360 degrees with respect to the grommet 48. Moreover, in various embodiments the guide tip 62 has three degrees of rotational freedom with respect to the grommet 48 such that the probe 20 correspondingly has three degrees of rotational freedom with respect to the grommet 48. In this configuration, the longitudinal position of the probe 20 is variable within the channel 64 of the probe guide 16 and the extent at which the probe 20 can be inserted into the incision (i.e. through the aperture 22 in the patch 12) is variable. The probe 20 is inserted within a channel 64 extending through the guide 16 to that the probe 20 can be inserted through the first aperture 22 of the patch 12 and into the incision to a target site, such as proximate a vagus nerve. In one non-limiting embodiment, the guide 16 is made of a rubber material.

The probe 20 includes a malleable shaft 70 and an electrode tip 72 and can optionally include one or more electrodes 74 (visible in FIG. 5) spaced about a circumference the shaft 70 proximal to the electrode tip 72. In some embodiments, the electrode tip 72 is blunt. The spherical or conic shaped blunted electrode tip 72 is atraumatic to blind tissue insertion. Additionally, the probe 20 can be insulated to the tip 72 (flush tip with only the electrode tip 72 uninsulated) for directional stimulation specificity. Tip 72 size/diameter can, in some embodiments, be in the range of 0.3 mm-3.0 mm. In some examples, the tip 72 size/diameter can be 0.5 mm-1.0 mm. In one embodiment, the electrode tip 72 is includes an uninsulated exposed 5 mm portion of the shaft 70 for wider stimulation range. But for the electrodes, the shaft 70 is electrically insulated. In some embodiments, the shaft 70 is made of a malleable material. Optionally, the shaft 70 can be made of a material that is opaque to x-ray and ultrasound imaging. In addition, a length of the shaft 70 an electrode tip 72 combined can be five inches or less. In some embodiments, the length of the combined shaft 70 an electrode tip 72 is arranged so that the combined shaft 70 an electrode tip 72 can extend at least four inches into the incision, which is typically is sufficient to reach almost all nerves. Although not shown, the shaft 70 may additionally include a battery and wiring for powering the electrode(s) as well as wireless communication capabilities so that electrode signals can be controlled and/or received from the nerve monitoring system 76 while omitting the wiring assembly 26. In the illustrated embodiment, all electrodes (e.g., 72) are electrically connected to the wiring assembly 26 (partially shown) in any known manner.

Figure 9:
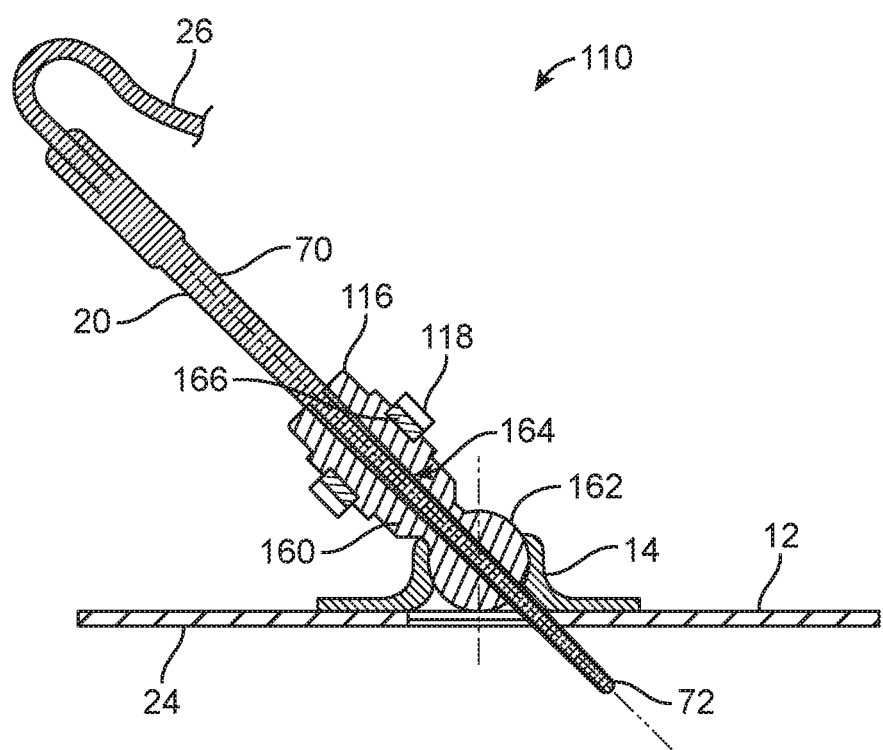
FIG. 9 is a cross-sectional view of the stimulation probe assembly of FIG. 8 as viewed along line A'-A'.
Figure 10:
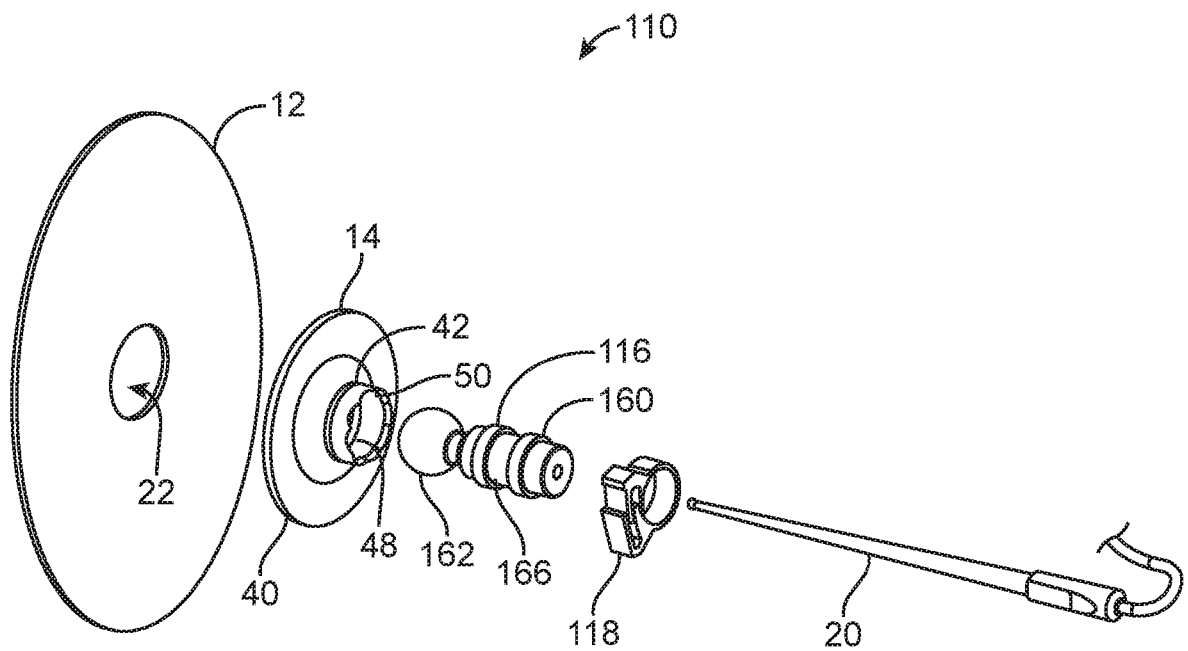
FIG. 10 is an exploded view of the stimulation probe assembly of FIGS. 7-9.
Figure 11:
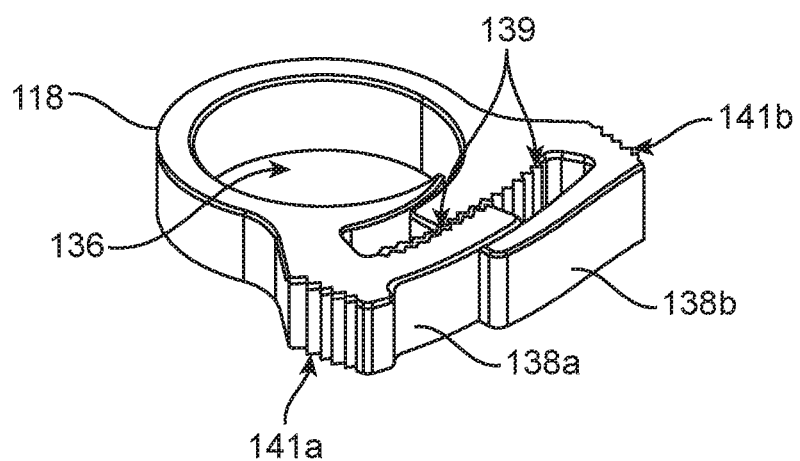
FIG. 11 is a perspective view of the clamp of FIGS. 7-10.

One of a variety of suitable clamps (e.g., clamp 18) is optionally provided in some embodiments for locking a depth and angle position of the probe 20 in place with respect to the guide socket 14. For example, an angle of the probe 20 can be defined as the angle between a central axis of the probe and the patch 12 (see also, FIG. 9 and related disclosure) and the depth can be defined as a shortest distance between the adhesive layer 24 of the patch 12 and the tip 72. In such embodiments, the clamp 18 can prevent injury to tissue. As is perhaps best shown in FIG. 3, once the probe 20 is in the desired position, the clamp 18 is secured and tightened around the guide socket 14, proximate the guide tip 62 to compressively retain the guide tip 62 and prevent the guide 16 from moving with respect to the socket 42. In one embodiment as shown, the clamp 18 is a quick lever clamp having an aperture 36 that can either be increased or decreased in diameter via lever 38. Other types of clamps are envisioned and a few examples are disclosed with respect to FIGS. 7-12.

Referring also now to FIGS. 7-11, which illustrate an alternate stimulation probe assembly 110. The stimulation probe assembly 110 of this embodiment is largely similar to that of FIGS. 1-6, as indicated with like reference numbers. It will be understood that the embodiment of FIGS. 7-11 is configured identically to and functions identically to the embodiment of FIGS. 1-6 except as explicitly stated. In this embodiment, an optional cup 130 is provided that defines a recess 132 for receiving the patch 12, guide socket 14, guide 116, clamp 118 and probe 20. The cup 130 can include an aperture 134 through which the wiring assembly 26 can extend.

In this embodiment, the previously disclosed clamp 18 is substituted with clamp 118. The clamp 118 can be used to lock a depth and angle position of the probe 20 in place with respect to the guide socket 14. For example, an angle ☐ of the probe 20 (FIG. 9) can be defined as the angle between a central axis of the probe and the patch 12 (and also the adhesive layer 24) and the depth can be defined as a shortest distance between the adhesive layer 24 or the patch 12 and the tip 72. The clamp 118 can form an aperture 136 in which the body 160 can be inserted. To adjust (e.g., increase or decrease) the diameter of the aperture 136, the clamp 118 includes a pair of arms 138a, 138b engaged with a plurality of corresponding threads 139. Each arm 139a, 139b includes a surface 141a, 141b that can be pressed to adjust the position of the arms 139a, 139b relative to one another. The surfaces 141a, 141b can optionally be textured to improve user grip. The clamp 118 of this embodiment, for example, can be secured and tightened around a body 160 of the guide 116 instead of at a guide tip 162. In this way, the clamp 118 compressively retains the probe 20 within a channel 164 of the guide 116 so that the probe 20 cannot move longitudinally within the channel 164. In some optional embodiments, the body 160 can be provided with a recess 166 for receiving and identifying a desired placement for the clamp 118. The clamp 118 is a snapper hose clamp. One suitable snapper hose clamp being the SNP1.5 Nylon Hose Clamp, Snapper Type available from HellermannTyton, Milwaukee, Wis.

Figure 12:
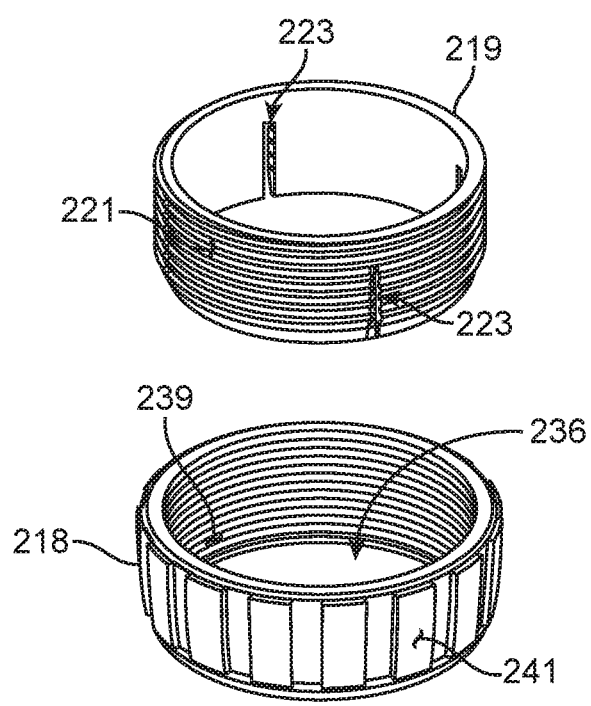
FIG. 12 is a perspective view of an alternate clamp that can be used as a substitute for any of the clamps disclosed herein.

In yet another embodiment shown in FIG. 12, it is envisioned that the clamps 18, 118 disclosed above can be replaced with a clamp 218, which is a knob-type clamp. The clamp 218 is generally ring-shaped and defines an aperture 236 that can be secured over a probe guide disclosed herein (e.g., probe guide 16, 116). In such embodiments, the probe guide 16, 116 is fitted with a guide ring 219 having a threaded outer surface 221 that corresponds to a threaded interior surface 239 of the clamp 218. In some embodiments, the guide ring 219 is positioned within the recess 166 formed in an outer surface of the probe guide 116 (the recess 166 is visible in FIG. 10). The guide ring 219 can optionally include one or more slits 223 (e.g., four equally spaced apart slits) so that the guide ring 219 is somewhat resilient and can more easily be positioned over the probe guide 16, 116. Once the probe 20 is positioned within the incision, proximate the desired nerve, the clamp 218 is threaded into the probe guide 16, 116 to lock the probe 20 in place via compressive forces applied by the clamp 218. Optionally, an outer surface 241 of the clamp 218 can be textured to improve user grip. Other clamp styles are envisioned and it will be apparent that other methods of securing the probe 20 in position will be apparent in view of the present disclosure.

In one example percutaneous method of the disclosure, a stimulation probe assembly is provided. The stimulation probe assembly can be of any of the type disclosed herein. An incision is made in a patient's skin, either prior to attachment of the patch to the patient's skin or after. In one embodiment, the incision is made with the blade shown in FIG. 4. Once the incision is formed and the patch is secured to the surface of the patient's skin either via adhesive or otherwise, the probe guide is secured to the adhesive patch. In alternate embodiments where the incision is formed prior to application of the adhesive patch, the patch and the probe guide can be pre-assembled and secured to the patient's skin as a unit. Similarly, the probe guide can come preassembled within the guide or can alternatively be assembled to the guide socket at a later point in time. The probe is inserted within the channel of the guide socket and then into the insertion. To place the electrode tip of the probe at a target location, movement of the probe, via the guide socket in one or more directions. In one embodiment, the target site is accessed inferior to incision. In various embodiments, the tissue is a nerve including a vagus nerve, cranial nerve, peripheral nerve or a nerve root. Once the desired placement is achieved, the depth and angle of the probe is locked with a clamp of the disclosure. As indicated above, if the wiring assembly includes a detachable connector, the detachable connected can be connected to the nerve monitoring system either prior to or after the probe is in position. If provided, the cup can optionally be secured over the probe, patch, probe guide, guide socket and clamp to prevent accidental bumping and movement of the probe. Then, the electrode can be energized via writing assembly to stimulate bioelectric tissue, such as a nerve (e.g., a vagus nerve, cranial nerve, peripheral nerve or nerve root), or the like.

In one example transcutaneous method of the disclosure the percutaneous method described above is followed with the exception of making an incision. Instead of guiding the probe through the incision, the probe is directed to the surface of the patient's skin and angled to apply the desired stimulation. In one embodiment, the electrode tip of the probe is positioned on a patient's skin, proximate a vagus nerve. In one embodiment, conductive gel is first applied to the skin and in some embodiments, the probe tip is pushed against the skin to identify a broad target location. As with the prior disclosed method, if the wiring assembly includes a detachable connector, the detachable connected can be connected to the nerve monitoring system either prior to or after the probe is in position. Also, if provided, the cup can optionally be secured over the probe, patch, probe guide, guide socket and clamp to prevent accidental movement of the probe during a procedure.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A stimulation probe assembly including:
a patch including a first aperture;
a guide socket including a proximal edge, a socket forming a grommet and the guide socket further including a flange having a second aperture; wherein the flange is positioned on the patch such that the first and second apertures are aligned;
a guide including a tip that is positioned within and rotatable within the guide socket; and
a probe interconnected with the guide; wherein the probe includes a shaft and at least one electrode;
a lock positioned around an outer surface of the grommet between the flange and the proximal edge, the lock configured to prevent movement of the guide within the guide socket when the lock is locked with respect to the guide socket;
wherein the tip has three degrees of rotational freedom with respect to the guide socket when the lock is unlocked with respect to the guide socket.

2. The stimulation probe assembly of claim 1, wherein the tip can rotate 360 degrees with respect to the guide socket when the lock is unlocked with respect to the guide socket.

3. The stimulation probe assembly of claim 1, wherein the probe includes a malleable shaft that is at least partially electrically insulated.

4. The stimulation probe assembly of claim 1, wherein the extent at which the probe can be inserted into the guide socket is variable when the lock is unlocked with respect to the guide socket.

5. A method of stabilizing a probe on a patient's skin, the method comprising:
providing a stimulation probe assembly including:
a patch including a first aperture;
a guide socket including a proximal edge, a socket forming a grommet and the guide socket further including a flange having a second aperture; wherein the flange is positioned on the patch such that the first and second apertures are aligned;
a guide including a tip that is positioned within and rotatable within the guide socket; and
a probe interconnected with the guide; wherein the probe includes a shaft and at least one electrode;
securing the patch to the patient's skin;
directing the probe through the guide, the guide socket and the patch; and
locking movement of the probe with respect to the guide socket with a lock positioned around an outer surface of the grommet between the flange and the proximal edge.

6. The method of claim 5, further comprising directing the step of forming an incision and directing the probe through the patient's skin.

7. The method of claim 5, wherein the patch is applied to the patient's skin adjacent a vagus nerve.

8. The method of claim 5, wherein the patch is applied to the patient's skin adjacent a cranial nerve.

9. The method of claim 5, wherein the patch is applied to the patient's skin adjacent a peripheral nerve.

10. The method of claim 5, wherein the patch is applied to the patient's skin adjacent a nerve root.

11. The method of claim 5, further comprising the step of moving the probe such that the tip rotates about the guide socket prior to the step of locking movement of the probe.

12. The method of claim 5, wherein the step of locking movement of the probe is achieved with a clamp.

13. The method of claim 5, wherein the step of securing the patch to the patient's skin is achieved with an adhesive.

14. The method of claim 5, wherein a grommet of the guide and the tip form a ball and socket joint.

15. The method of claim 5, further comprising the step of positioning a cup over the probe.

16. The method of claim 15, wherein the cup includes a recess in which the patch, probe guide and guide socket are positioned.

17. The method of claim 5, further comprising moving the probe about three degrees of rotational freedom with respect to the guide socket prior to the step of locking movement of the probe.

18. The method of claim 5, wherein during the step of locking, the guide socket is entirely positioned outside of the first aperture.

19. The stimulation probe assembly of claim 1, wherein the lock is a clamp positioned circumferentially around both the guide socket and the tip when the probe is inserted within the first aperture.

20. The stimulation probe assembly of claim 1, wherein the proximal edge includes at least one divot.

* * * * *